United States Patent [19]

Thomas

[11] 4,178,437

[45] Dec. 11, 1979

[54] 1-N-KANAMYCIN DERIVATIVES

[75] Inventor: Michael B. Thomas, Deal, England

[73] Assignee: Pfizer Inc., New York, N.Y.

[21] Appl. No.: 924,515

[22] Filed: Jul. 14, 1978

[30] Foreign Application Priority Data

Aug. 18, 1977 [GB] United Kingdom ............... 34808/77

[51] Int. Cl.$^2$ ...................... A61K 31/71; C07H 15/22
[52] U.S. Cl. ...................... 536/10; 424/180; 536/17 R
[58] Field of Search ................................... 536/10, 17

[56] References Cited

U.S. PATENT DOCUMENTS

| | | |
|---|---|---|
| 3,350,387 | 10/1967 | Vanderhaeghe ........................ 536/17 |
| 4,029,882 | 6/1977 | Wright ................................... 536/10 |
| 4,044,123 | 8/1977 | Daniels et al. ......................... 536/10 |
| 4,065,615 | 12/1977 | Horii et al. ............................. 536/10 |

*Primary Examiner*—Johnnie R. Brown
*Attorney, Agent, or Firm*—Connolly and Hutz

[57] ABSTRACT

3-N-formyl derivatives of 3″,6′-di-N-acyl-kanamycin A and 2′,3″,6′-tri-N-acyl-kanamycin B, process for their preparation, and their use as intermediates for production of antibacterially active 1-N-(substituted) derivatives of kanamycins A and B by alkylation and subsequent removal of the formyl and acyl groups.

4 Claims, No Drawings

1-N-KANAMYCIN DERIVATIVES

BACKGROUND OF THE INVENTION

1. Field of the Invention

This invention relates to a novel process for the preparation of aminoglycoside antibiotics and with novel intermediates for use in such process, and is particularly concerned with a process for the preparation of 1-N-alkyl-substituted-kanamycin derivatives and with selectively N-protected kanamycin derivatives as intermediates for use in the process.

2. Description of the Prior Art

A variety of N-acyl derivatives of kanamycins A and B are reported in the art. Belgian Pat. No. 817,546 describes preparation of N-formyl derivatives of kanamycins A and B formylated on all but the 1-amino group; said compounds being produced by selective hydrolysis of the formyl group from the 1-amino group of fully formylated kanamycins A and B by means of dilute aqueous ammonia.

British Pat. No. 1,464,401 describes 1-N-alkyl derivatives of the kanamycins and Belgian Pat. No. 851,777 broadly discloses preparation of 1-N-(ω-amino-2-hydroxyalkyl) derivatives of kanamycins A and B by reductive alkylation of selectively protected kanamycins A and B, including 3,3",6'-tri-N-formyl kanamycin A and 2',3,3", 6'-tetra-N-formyl kanamycin B.

However, none of these references specifically identifies or specifically teaches preparation of 3",6'-di-N-acyl-3-N-formyl kanamycin A derivatives or 2',3",6'-tri-N-acyl-3-N-formyl derivatives of kanamycin B wherein acyl represents $C_{2-4}$ alkanoyl or benzoyl. Further, the preparation of such derivatives by selective hydrolysis of the corresponding 3",6'-di-N-acyl-1,3-di-N-formyl kanamycin A or 2',3",6'-tri-N-acyl-1,3-di-N-formyl kanamycin B derivatives is not taught by the art.

Examples of such 1-N-alkyl-substituted kanamycin derivatives are described in British patent specification No. 1,464,401; others are described in Belgian Pat. No. 855,709.

SUMMARY OF THE INVENTION

In order to prepare such compounds from the readily available fermentation product kanamycin, it is desirable to protect all the amino groups other than the 1-amino group. Alkylation may then be effected preferentially on the amino group on the 1-position and isolation of the final 1-N-substituted product is thereby simplified. It is an object of this present invention to provide an improved process for the preparation of 1-N-substituted kanamycin derivatives by providing such selectively N-protected intermediates.

Thus, according to the invention there is provided a process for preparing compounds of the formula:

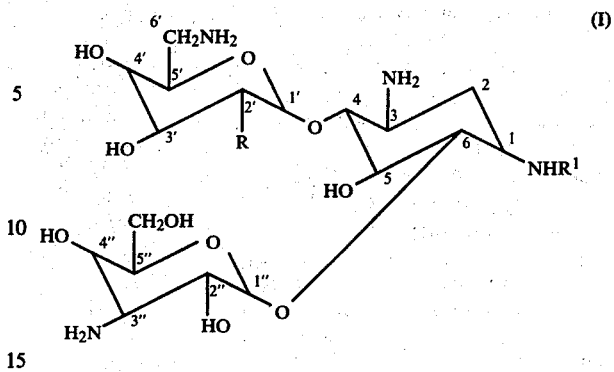

wherein R is selected from the group consisting of amino and hydroxyl; and $R^1$ is selected from the group consisting of lower alkyl, $C_2$ to $C_6$ mono- or polyhydroxyalkyl with the proviso that the carbon atom of the alkyl group attached to the nitrogen atom be free of hydroxyl substitution; and ω-amino-2-hydroxyalkyl having from 3 to 5 carbon atoms, which comprises (1) alkylating a compound of the formula:

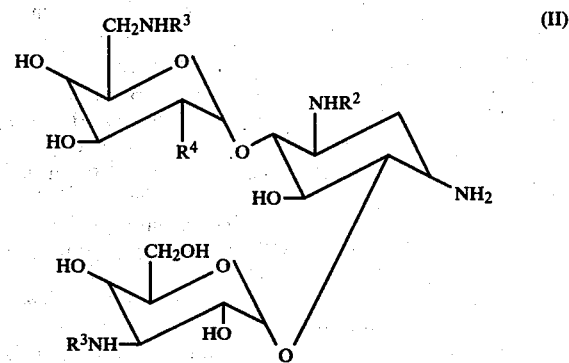

wherein $R^2$ is formyl; $R^3$ is selected from the group consisting of $C_2$ to $C_4$ alkanoyl and benzoyl; and $R^4$ is selected from the group consisting of hydroxy and $NHR^3$; to produce a compound of the formula:

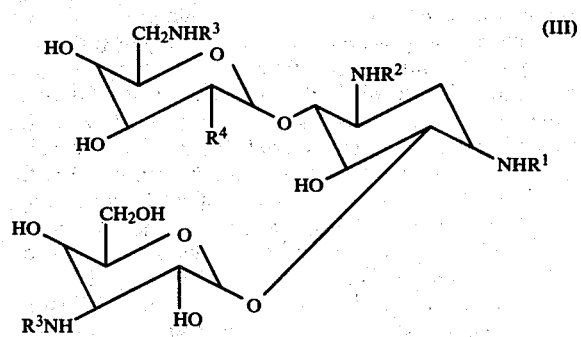

wherein $R^1$, $R^2$, $R^3$ and $R^4$ are as defined above; (2) removing groups $R^2$ and $R^3$; and (3) recovering the compound of formula (I).

In this specification the term lower alkyl indicates that such a group contains from 1 to 6 carbon atoms and may be straight or branched chain. Particular examples of substituted-lower alkyl groups $R^1$ are the [S]-4-amino-2-hydroxybutyl and 1,3-dihydroxyprop-2-yl groups. The blocking group $R^3$ is preferably an acetyl group.

This process for the preparation of compounds of formula (I) comprises as an initial step alkylation of a compound of formula (II) in order to introduce the substituent $R^1$ onto the amino group at the 1-position. Such a reaction may be performed in a number of ways well known to those skilled in the art. For example, alkylation may be achieved by reductive alkylation using an appropriate aldehyde or ketone, or a compound such as described in Belgian Pat. No. 851,777.

The second step of the process comprises removal of the blocking groups $R^3$ from the 2'-amino group, if present, and the 6' and 3"-amino groups and also the formyl group on the 3-amino group. In some instances where the 1-N-substituent itself bears an amino substituent group it may be desirable to protect this group during the course of the process and it will then be necessary to remove this amino-blocking group as well in the final step of the process. There are various conditions for completely removing amino-blocking groups, well known to those skilled in the art, and they will naturally depend on the nature of the protecting group employed and the environment of the protected amine. The medium employed may be anhydrous or aqueous and in particular instances it may be acidic or basic to various strengths. For example, the benzyl group, when present, can be removed by catalytic hydrogenolysis in a conventional manner in the presence of a palladium catalyst. The alkanoyl or benzoyl blocking groups may generally be removed by hydrolysis under mild basic conditions, for example by treatment with dilute sodium hydroxide at 65° C. for several hours. These conditions also remove the formyl group. The product (I) may finally be purified, if desired, by conventional techniques, for example, by crystallization or by chromatography.

The process is exemplified by the preparation of 1-N-[(S)-4-amino-2-hydroxybutyl]kanamycin A. In this case the protected kanamycin intermediate of formula (II) wherein $R^4$ is a hydroxyl group and $R^3$ is an acetyl group is alkylated by a reductive alkylation using an appropriate aldehyde or a compound as described in Belgian Pat. No. 851,777. Thus, 3-benzyl-6-(S)-dihydroxymethyltetrahydro-1,3-oxazin-2-one may be used and the reductive alkylation may be performed using sodium borohydride or preferably sodium cyanoborohydride as reducing agent. Excess aldehyde (or other compound) and reducing agent may be used to ensure complete reaction of the free 1-amino group. Suitable solvents are aqueous methanol or aqueous dioxan; dimethylformamide or dimethylsulfoxide are also suitable. An acid e.g. acetic acid may also be added with advantage. The reaction is generally performed at room temperature and is usually complete within 5 or 6 hours. The crude product may be isolated by evaporation of the solvent and may be further purified, if desired, by recrystallization or chromatography. Generally, however, it will be more convenient to use the crude product directly in the next stage of the process. Thus the crude product is dissolved in dilute sodium hydroxide and heated at 65° C. for a period of about 5 hours to effect removal of the formyl and acetyl blocking groups. After neutralization, the product, preferably separated from the inorganic material, is subjected to a conventional catalytic hydrogenation to remove the benzyl protecting group. A period of 4 or 5 hours at 60° C. and a pressure of 60 p.s.i. is generally sufficient to effect complete removal of the benzyl group and the product is finally worked up in a conventional manner and purified if necessary by ion exchange chromatography to give the final product. Since there is only one reactive amino group in the starting material of formula (II) the final product consists substantially of the required 1-N-substituted isomer and the difficult separation of closely related isomers is thereby avoided.

The reaction may also be performed in an exactly analogous manner using 2',3",6'-tri-N-acetyl-3-formylkanamycin B to provide the corresponding 1-N-substituted kanamycin B derivative.

The alkylation reaction may also be performed using a hydroxy-substituted aldehyde or ketone to give 1-N-hydroxyalkyl substituted kanamycin derivatives such as are described in Belgian Pat. No. 855,709. Thus, for example, when 1,3-dihydroxy acetone is used in the process the product of formula (I) is obtained wherein $R^1$ is a 1,3-dihydroxyprop-2-yl group.

The compounds of formula (II) are themselves novel compounds according to the invention. They may be prepared from 3",6'-di-N-acyl-kanamycin A or 2',3",6'-tri-N-acyl-kanamycin B by a reaction which involves first formylation of the remaining unsubstituted 1- and 3-amino groups and secondly a selective hydrolysis step which has been found, surprisingly, to effect the removal of the formyl group from the 1-amino position while leaving the formyl group on the 3-position untouched.

The preparation of suitable acyl-kanamycin derivatives substituted on the 3" and 6' amino groups in kanamycin A and additionally on the 2' amino group in kanamycin B with a $C_2$ to $C_4$ alkanoyl group or a benzoyl group is described in Belgian Pat. No. 853,564. For example, the preparation of 3",6'-di-N-acetyl-kanamycin A is described via a selective O to N acetyl migration reaction. Other derivatives may be prepared in a similar manner.

The formylation reaction may be performed in a number of different ways, well known to those skilled in the art. For example, formylation may be achieved using a mixture of formic and acetic anhydrides but we have found that the reaction may conveniently be performed using 4-nitrophenylformate. Suitable solvents for the reaction are aqueous dioxan, aqueous tetrahydrofuran or dimethylformamide, and the reaction is performed by adding excess (e.g. a three fold excess) of 4-nitrophenylformate, in portions, to the kanamycin derivative. A base is preferably added to aid the reaction and an organic base, e.g. triethylamine may be employed for this purpose. At least one equivalent of base is preferably added for each reactive amino group. The formylation reaction is generally complete within 24 hours at room temperature and the product may then be isolated by conventional techniques, e.g. by evaporation of the solvent or by precipitation and may be further purified if desired.

The selective hydrolysis stage is performed with the 1,3-di-N-formyl product dissolved in water or in an aqueous organic solvent, e.g. aqueous dioxan or aqueous tetrahydrofuran and the pH of the solution is carefully adjusted to within the range 12.0–12.5 with an alkali, e.g. by adding dilute sodium or potassium hydroxide. The solution is stirred at room temperature for several days, the course of the reaction being followed by thin-layer chromatography, until conversion to the desired 3-N-formyl derivative of formula (II) is complete. The solution is then neutralized by addition of acid, or more conveniently by adding an ion-exchange resin in the hydrogen-ion form. This has the advantage of preventing a build-up of inorganic material in solution and has the added advantage that any by-product in which both the 1- and 3-formyl groups have been cleaved is adsorbed onto the resin. The product is finally isolated by conventional techniques, e.g. by evaporation to a low volume and precipitation with an organic solvent, e.g. isopropanol. Further purification if desired may be achieved by chromatography but in general the product is sufficiently pure for use in the preparation of compounds of the formula (I) directly.

The process for the preparation of compounds of the formula (II) may be performed using 3",6'-di-N-acetyl kanamycin A to give the compound of formula (II) wherein $R^3$ is acetyl and $R^4$ is a hydroxy group. Similarly, 2',3",6'-tri-N-acetyl-kanamycin B may be used to give the compound of formula (II) wherein $R^4$ is a group $NHR^3$ and $R^3$ is acetyl.

The invention is illustrated by the following Examples in which Examples 1 and 3 are examples of preparation of novel intermediates of the formula (II) and Examples 2, 4, 5, and 6 are examples of the novel process for preparation of antibacterially active compounds of formula (I).

Thin layer chromatography was performed on silica plates using the solvent system stated. The spots were visualized after drying the plates by spraying with a 5% solution of t-butyl-hypochlorite in cyclohexane, drying the plates at 100° C. for 10 minutes in a ventilated oven, cooling and spraying with starch-potassium iodide solution.

Thin layer electrophoresis was performed on 20 cm. silica plates with a potential difference of 900 volts applied for 45 minutes. The electrolyte was a mixture of formic and acetic acids giving a pH value of 2, detection was performed as above.

EXAMPLE 1

Preparation of
3",6'-Di-N-acetyl-3-N-formyl-kanamycin A (A) 4-Nitrophenylformate (6.88 g.) was added portionwise over 45 minutes to a suspension of 3",6'-di-N-acetyl-kanamycin A (3.9 g.) in water (21 ml.) and tetrahydrofuran (21 ml.) containing triethylamine (6.91 g.). The reaction was stirred at room temperature overnight and then evaporated to low volume replacing the final traces of water by azeotropic distillation with isopropanol (final volume 35 ml.). 3",6'-Di-N-acetyl-1,3-di-N-formyl-kanamycin A (2.41 g.) precipitated from the solution and was filtered and dried in vacuum at 50° C.

On thin layer electrophoresis (pH=2) the compound gave a value of 0.09 with respect to kanamycin A. On thin layer chromatography (t.l.c.) using methanol, ethyl acetate, ammonia, water (40:40:1:30) as eluant it gave $R_f$ 0.42. The proton n.m.r. spectrum showed signals at $\delta = 7.96$ p.p.m. (formyl proton), 8.02 p.p.m. (formyl proton) and 2.02 p.p.m. (6 acetyl protons).

(b) The product from (A) (2.4 g.) was dissolved in water (72 ml.) and the pH of the solution was adjusted to 12.0–12.5 with 2 N sodium hydroxide solution (2.0 ml.). The solution was stirred at room temperature for 7 days maintaining the pH between 12.0 and 12.5 and was then neutralized by the addition of Amberlite IR120 ion exchange resin (H+ form) (10 ml.). The resin was filtered and the filtrate was concentrated to low volume, the final traces of water being removed by displacement with dimethylformamide (5 ml.) at reflux. Isopropanol (30 ml.) was then added slowly to the dimethylformamide solution and the precipitate of 3",6'-di-N-acetyl-3-N-formyl-kanamycin A (1.75 g.) was filtered and dried in vacuum at 40° C.

The compound was pure enough for use in the next stage of the process. A sample was further purified by chromatography on the weakly acidic cation exchange resin sold under the trademark CM Sephadex C25 (NH$_4$+ form) using 0.1 M ammonium hydroxide solution as eluant. (It is a carboxymethyl derivative of the polysaccharide dextran which is cross-linked to give a three-dimensional network). The carboxymethyl groups are attached to the glucose units of the polysaccharide chains by ether linkages. It gave a C-13 n.m.r. spectrum in full agreement with the required structure and which confirmed mono formylation of the 3-amino group. Thin layer electrophoresis (pH=2) gave a value of 0.43 with respect to kanamycin A. On t.l.c. using methanol, ethyl acetate, ammonia, water (40:40:1:30) as eluant the compound gave an $R_f$ value of 0.23.

In like manner, the following compounds are prepared by substituting the appropriate 3",6'-di-N-acylkanamycin A as reactant for 3",6'-di-N-acetyl-kanamycin A:

3",6'-di-N-propionyl-3-N-formyl-kanamycin A
3",6'-di-N-butyryl-3-N-formyl-kanamycin A
3",6'-di-N-benzoyl-3-N-formyl-kanamycin A

EXAMPLE 2

Preparation of
1-N-[(S)-4-amino-2-hydroxybutyl]-kanamycin A

Sodium cyanoborohydride (0.21 g.) in water (40 ml.) was added to the title compound of Example 1, 3",6'-di-N-acetyl-3-N-formyl-kanamycin A (2.0 g.), 3-benzyl-6-(S)-dihydroxymethyl-tetrahydro-2 H-1,2-oxazin-2-one (2.38 g.) and copper sulfate (0.1 g.) in water (66 ml.) and methanol (322 ml.) over 5 hours. The reaction mixture was evaporated to dryness under reduced pressure and the residue was treated with water (25 ml.) and methylene chloride (25 ml.). The aqueous phase was evaporated to dryness and the residue was heated with 3 N sodium hydroxide solution (20 ml.) at 65°–70° C. for 4 hours. The solution was cooled and neutralized with concentrated hydrochloric acid using good fume extraction (HCN given off) and passed down a 600 ml. column of a carboxylic cationic exchange resin (NH$_4$+ form) derived from methyacrylic acid cross-linked with divinylbenzene, sold under the trademark Amberlite CG-50 (NH$_4$+ form), eluting the inorganics with water, and the aminoglycoside materials with 0.2 N ammonium hydroxide solution.

The aminoglycoside fractions were evaporated to dryness and the residue was dissolved in a mixture of methanol (13 ml.), acetic acid (13 ml.) and water (13 ml.) and hydrogenated over 5% palladium on charcoal (0.4 g.) at 60° C. and 60 p.s.i. for 4 hours. The catalyst was filtered and the filtrate was evaporated to dryness. The residue was dissolved in water (20 ml.) and chromatographed on a 200 ml. CG-50 (NH$_4$+ form) ion exchange column using ammonium hydroxide solution (0.25–1.0 M) as eluant. Evaporation of the appropriate fractions gave 1-N-[(S)-4-amino-2-hydroxybutyl]kanamycin A (0.75 g., 37%) identical on thin layer chromatography and thin layer electrophoresis with an authentic sample.

Repetition of this procedure but substituting the remaining 3",6'-di-N-acyl-3-N-formyl-kanamycin A derivatives of Example 1 for the di-N-acetyl derivative affords the same product.

EXAMPLE 3

Preparation of
2′,3″,6′-tri-N-acetyl-3-N-formyl-kanamycin B (A) Benzyl chloroformate (128 g.) was added over a period of 10 minutes to a solution of kanamycin B sulfate (80.5 g.) and sodium carbonate (76 g.) in water (400 ml.), and the solution was stirred for 1 hour at room temperature. The precipitate was collected by filtration, washed with water, with dilute hydrochloric acid and with water and dried to yield penta-N-benzyloxycarbonyl-kanamycin B (yield 125.7 g.).

(B) Penta-N-benzyloxycarbonyl-kanamycin B (230.8 g.) was added portionwise over 15 minutes to a stirred solution of acetic anhydride (189 ml.) in pyridine (346 ml.) and dichloromethane (346 ml.) and the suspension was stirred at room temperature for 48 hours. The solution was poured into a mixture of dichloromethane (1.5 liters) and water (2.3 liters). The organic phase was separated and washed with dilute hydrochloric acid (pH 4) and with water. The solvent was evaporated to a volume of 0.75 liter and the solution poured into diether ether (4 liters). The precipitate of tetra-O-acetyl-penta-N-benzyloxycarbonylkanamycin B was collected by filtration and dried under vacuum (yield 244.8 g., 92.6%).

(C) A solution of tetra-O-acetyl-penta-N-benzyloxycarbonyl-kanamycin B (33.0 g.) in tetrahydrofuran (132 ml.) water (66 ml.) and acetic acid (3.3 ml.) was hydrogenated over 5% palladium on charcoal catalyst (3.3 g.) at 50° C. and 50 p.s.i. for 7 hours. The catalyst was removed by filtration and the filtrate was concentrated to a volume of 25 ml. The residue was treated with ammonium hydroxide (7 N, 81.5 ml.) and stirred overnight at room temperature. The solution was evaporated to dryness and the residue chromatographed on a column of Amberlite CG-50 ion-exchange resin in the ammonium ion form (2 liters) eluting with water and then with 0.01 aqueous ammonia. Fractions containing the desired product were combined and evaporated to yield 2′,3″,6′-tri-N-acetyl-kanamycin B (9.37 g., 61.6%), m.p. 191°–198° C. (decomp.) λmax. (KBr) 1650, 1550 cm$^{-1}$, R$_f$ 0.11 (6:3:1:2 methanol, diethyl ether, water, 0.880 aqueous ammonia), R$_f$ 0.11 (40:40:30:1 methanol, ethyl acetate, water, 0.880 aqueous ammonia).

(D) p-Nitrophenylformate (153.1 g.) was added portionwise over 40 minutes to a cooled solution of 2′,3″,6′-tri-N-acetyl-kanamycin B (93 g.) in a mixture of water (465 ml.), tetrahydrofuran (558 ml.) and triethylamine (154 g.). The reaction mixture was stirred at room temperature overnight and then concentrated to a low volume under reduced pressure. The aqueous concentrate was diluted with isopropanol to precipitate the product, the residual water being removed by azeotropic distillation with isopropanol. The product was finally collected by filtration, washed with isopropanol and dried under vacuum to yield 2′,3″,6′-tri-N-acetyl-1,3-di-N-formyl kanamycin B (89.2 g.), m.p. 310°–318° C. (decomp.) λmax. (KBr) 1665, 1545 cm$^{-1}$, R$_f$ 0.49 (6:3:1:2 methanol, diethyl ether, water, 0.880 aqueous ammonia), R$_f$ 0.54 (40:40:30:1 methanol, ethyl acetate, water, 0.880 aqueous ammonia).

(E) A solution of 2′,3″,6′-tri-N-acetyl-1,3-di-N-formyl kanamycin B (86.9 g.) in water (2.61 liters) was taken to pH 12 to 12.5 with 10 N sodium hydroxide solution. The reaction was kept at room temperature for 4 days readjusting the pH of the solution to 12 with aqueous sodium hydroxide as necessary, and the solution was then neutralized by the addition of Amberlite IR 120 resin (H+ form), a cationic ion-exchange resin comprising a sulfonated polystyrene matrix cross-linked with 3–5% divinylbenzene. The mixture was filtered and the filtrate was chromatographed on Amberlite 200, a macroreticular sulfonated polystyrene-divinylbenzene cationic exchange resin (ammonium-ion form, 5.5 liters), eluting with water and then with 0.1 N aqueous ammonium hydroxide. Evaporation of the appropriate fractions gave 2′,3″,6′-tri-N-formyl kanamycin B (55.4 g.), m.p. 266°–268° C. (decomp.) λmax. (KBr) 1665, 1555 cm$^{-1}$, R$_f$ 0.49 (40:40:30:1 methanol, ethyl acetate, water, 0.880 aqueous ammonia). The structure was confirmed by C-13 n.m.r. spectroscopy.

By means of the above procedures, but using the appropriate acyl anhydride in place of acetic anhydride, the following compounds are prepared:
2′,3″,6′-tri-N-propionyl-3-N-formyl-kanamycin B
2′,3″,6′-tri-N-butyryl-3-N-formyl-kanamycin B
2′,3″,6′-tri-N-benzoyl-3-N-formyl-kanamycin B

EXAMPLE 4

Preparation of 1-N-(1,3-Dihydroxyprop-2-yl)
Kanamycin B

A solution of 2′,3″,6′-tri-N-acetyl-3-N-formyl kanamycin B (the title compound of Example 3) (8.8 g.) in methanol (880 ml.) and water (176 ml.) was treated with 1,3-dihydroxyacetone (4.0 g.) and sodium cyanoborohydride (3.9 g.) and the pH of the resulting solution adjusted to 6.5 with 5 N hydrochloric acid. The solution was heated under reflux for 18 hours, cooled and further 1,3-dihydroxyacetone (4.0 g.) and sodium cyanoborohydride (3.9 g.) were added. The pH was readjusted to 5.5 with hydrochloric acid and the solution was heated under reflux for a further 6 hours. The methanol was removed under reduced pressure and the aqueous concentrate was chromatographed on a column of Amberlite 200 ion-exchange resin in the ammonium ion form eluting with water. Fractions containing the required 2′,3″,6′-tri-N-acetyl-3-N-formyl-1-N-(1,3-dihydroxyprop-2-yl) kanamycin B were combined and concentrated under reduced pressure to a volume of 40 ml.

The concentrate was treated with 10 N aqueous sodium hydroxide (40 ml.) and the mixture was heated on a steam bath for 16 hours. The cooled solution was neutralized with concentrated hydrochloric acid, water added to a volume of 1 liter and the mixture chromatographed on a column of Amberlite 200 ion-exchange resin (ammonium-ion form, 3 liters). The column was washed with water to remove inorganics and then with 1 N aqueous ammonia to elute the aminoglycoside materials. The crude product was re-chromatographed on Amberlite CG-50 ion-exchange resin (ammonium-ion form, 2 liters) eluting with water, 0.05 N aqueous ammonium hydroxide and finally 0.1 N aqueous ammonium hydroxide. Evaporation of appropriate fractions gave 1-N-(1,3-dihydroxyprop-2-yl) kanamycin B (3.2 g.) identical on thin layer chromatography with a reference sample.

Substitution of the remaining 2′,3″,6′-tri-N-acyl-3-N-formyl-kanamycin B derivatives of Example 3 for the tri-N-acetyl derivative in the above procedure provides the same product.

EXAMPLE 5

Following the reductive alkylation procedure of Example 4, the 1-N-kanamycin products having the formula shown below wherein $R^2$ and $R^3$ are hydrogen and $R^4$ and $R^1$ are as indicated are prepared from appropriate kanamycin reactants of said formula wherein $R^2$ is formyl, $R^3$ and $R^4$ have the values indicated below and from appropriate aldehydes and ketones.

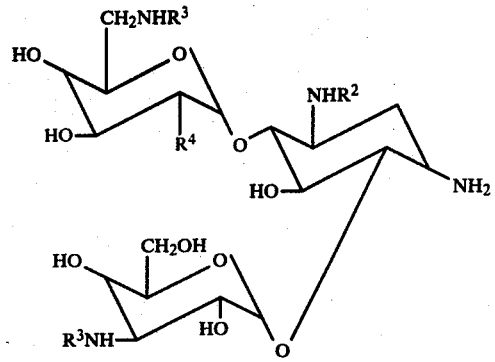
(II)

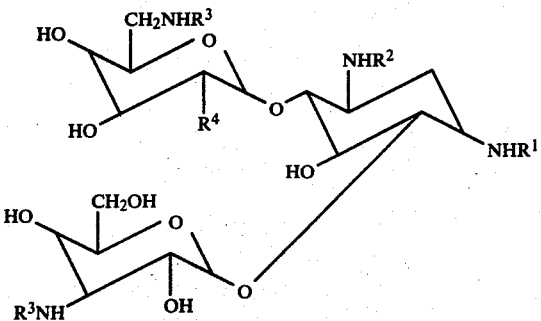

| Aldehyde or Ketone Reactant | $R^1$ | Kanamycin Reactant $R^3$ | $R^4$ |
|---|---|---|---|
| D-glyceraldehyde | (S)-$CH_2CHOH$—$CH_2OH$ | $COCH_3$ | OH |
| D-glyceraldehyde | (S)-$CH_2$—CHOH—$CH_2OH$ | $COCH_3$ | $NHCOCH_3$ |
| D-erythrose | (S) (R)-$CH_2$—$(CHOH)_2$—$CH_2OH$ | $COCH_3$ | OH |
| D-ribose | (S) (S) (R)-$CH_2$—$(CHOH)_2$—CHOH | $COCH_3$ | $NHCOCH_3$ |
| D-ribose | (S) (S) (R)-$CH_2$—$(CHOH)_3$—$CH_2OH$ | $COC_2H_5$ | OH |
| 2-deoxy-D-ribose | (S) (R)-$CH_2$—$CH_2$—$(CHOH)_2$—$CH_2OH$ | $COC_3H_7$ | $NHCOC_3H_7$ |
| 2-deoxy-D-ribose | (S) (R)-$CH_2$—$CH_2$—$(CHOH)_2$—$CH_2OH$ | $COC_6H_5$ | OH |
| D-arabinose | (R) (S) (R)-$CH_2$—$(CHOH)_3$—$CH_2OH$ | $COCH_3$ | OH |
| D-xylose | (S) (R) (R)-$CH_2$—$(CHOH)_3$—$CH_2OH$ | $COC_6H_5$ | $NHCOC_6H_5$ |
| L-xylose | (R) (S) (S)-$CH_2$—$(CHOH)_3$—$CH_2OH$ | $COCH_3$ | $NHCOCH_3$ |
| L-xylose | (R) (S) (S)-$CH_2$—$(CHOH)_3$—$CH_2OH$ | $COCH_3$ | OH |
| L-ribose | (R) (R) (S)-$CH_2$—$(CHOH)_3$—$CH_2OH$ | $COCH_3$ | OH |
| D-glucose | (S) (R) (R) (R)-$CH_2$—$(CHOH)_4$—$CH_2OH$ | $COCH_3$ | OH |
| D-glucose | (S) (R) (R) (R)-$CH_2$—$(CHOH)_4$—$CH_2OH$ | $COC_3H_7$ | $NHCOC_3H_7$ |
| L-glyceraldehyde | (R)-$CH_2$—CHOH—$CH_2OH$ | $COC_6H_5$ | OH |
| 1,3-dihydroxyacetone | —$CH_2(CH_2OH)_2$ | $COCH_3$ | OH |
| hydroxyacetone | —$CH_2(CH_2OH)CH_3$ | $COC_2H_5$ | $NHCOC_2H_5$ |
| formaldehyde | —$CH_3$ | $COC_6H_5$ | OH |
| butyraldehyde | —$(CH_2)_3CH_3$ | $COCH_3$ | OH |
| isovaleraldehyde | —$(CH_2)_2CH(CH_3)_2$ | $COCH_3$ | $NHCOCH_3$ |
| n-caproaldehyde | —$(CH_2)_5CH_3$ | $COC_3H_7$ | $NHCOC_3H_7$ |
| methyl ethyl ketone | —$CH_2(CH_3)CH_2CH_3$ | $COCH_3$ | $NHCOCH_3$ |
| hexanone-2 | —$CH_2(CH_3) (CH_2)_3CH_3$ | $COC_2H_5$ | OH |
| diethyl ketone | —$CH_2(CH_2CH_3)_2$ | $COCH_3$ | $NHCOCH_3$ |

EXAMPLE 6

1-N-[(S)-3-Amino-2-hydroxypropyl]-kanamycin A

The procedure of Example 2 is repeated but using 3-benzyl-5-(S)-dihydroxymethyl-1,3-oxazolidin-2-one as reactant in place of 3-benzyl-6-(S)-dihydroxymethyl-tetrahydro-2 H-1,3-oxazin-2-one to give the title compound.

What is claimed is:

1. A compound of the formula:

wherein $R^2$ is formyl; $R^3$ is selected from the group consisting of $C_2$ to $C_4$ alkanoyl and benzoyl; and $R^4$ is selected from the group consisting of hydroxy and $NHR^3$.

2. A compound according to claim 1 wherein $R^3$ is acetyl.

3. 3'',6'-Di-N-acetyl-3-N-formyl-kanamycin A, the compound according to claim 2 wherein $R^4$ is hydroxy.

4. 2',3'',6'-Tri-N-acetyl-3-N-formyl-kanamycin B, the compound according to claim 2 wherein $R^4$ is NH-acetyl.

* * * * *